United States Patent [19]
Woog et al.

[11] Patent Number: 5,324,749
[45] Date of Patent: Jun. 28, 1994

[54] PHARMACEUTICAL AQUEOUS SOLUTION OF 4-[2-(BENZENE-SULPHONYLAMINO)-ETHYL]-PHENOXYACETIC ACID

[75] Inventors: Heinrich Woog, Laudenbach; Werner Gruber, Birkenau; Werner Heller, Grunstadt; Fritz Demmer, Hirschberg-Leutershausen, all of Fed. Rep. of Germany

[73] Assignee: Boehringer Mannheim GmbH, Mannheim, Fed. Rep. of Germany

[21] Appl. No.: 930,592

[22] PCT Filed: Mar. 26, 1991

[86] PCT No.: PCT/EP91/00578
§ 371 Date: Nov. 4, 1992
§ 102(e) Date: Nov. 4, 1992

[87] PCT Pub. No.: WO91/15202
PCT Pub. Date: Oct. 17, 1991

[30] Foreign Application Priority Data
Apr. 2, 1990 [DE] Fed. Rep. of Germany ....... 4010536

[51] Int. Cl.$^5$ ............................................. A01N 37/12
[52] U.S. Cl. ..................................................... 514/562
[58] Field of Search ......................................... 514/562

[56] References Cited

FOREIGN PATENT DOCUMENTS

0004011  9/1979  European Pat. Off. .
0083775  7/1983  European Pat. Off. .
0332306  9/1989  European Pat. Off. .

OTHER PUBLICATIONS

Kopia, G. A. et al., The J. of Pharmacology and Experimental Therapeut. 250 (3) Sep. 1989.

*Primary Examiner*—Paul J. Killos
*Attorney, Agent, or Firm*—Nikaido, Marmelstein, Murray & Oram

[57] ABSTRACT

The present invention concerns a storage-stable, aqueous solution of 4-[2-(benzenesulphonylamino)-ethyl]-phenoxyacetic acid for pharmaceutical purposes.

11 Claims, No Drawings

PHARMACEUTICAL AQUEOUS SOLUTION OF 4-[2-(BENZENE-SULPHONYLAMINO)-ETHYL]-PHENOXYACETIC ACID

The subject of the present invention is a stable pharmaceutical aqueous solution of 4-[2-(benzenesulphonylamino)-ethyl]-phenoxyacetic acid. This solution is used as injection or infusion solution or, in concentrated form, as additive to infusion solutions.

The active material 4-[2-(benzenesulphonylamino)-ethyl]-phenoxyacetic acid and its preparation is described in EP-A-004,011 as Example 1. This compound is especially suitable for the preparation of medicaments for the treatment of diseases which are involved with an increased thrombocyte aggregation. The active material displays a significant lipid-sinking action and possesses an outstanding inhibiting action on the thrombocyte aggregation.

Diseases which can be treated with this active material are, for example, atherosclerotic diseases of the blood vessel system, diseases of the kidney, as well as the treatment of shock lung. Furthermore, in this connection, the following indications come into question: prevention of the damaging of the microcirculation due to radiation therapy (e.g. in the kidney); treatment of hearing precipitation; prevention of reocclusion in the case of by-pass operations, in the case of coronary and peripheral thrombolysis, as well as lysis in the venous circulation, in combination with fibrinolytics (e.g. urokinase, streptokinase, tPA and its derivatives); prevention or reduction of the thrombocyte decrease in the case of dialysis or extracorporeal circulation, as well as keeping open of arterial and venous cannulae and catheters, also together with prostacyclin and prostacyclin mimetics; prevention of the side effects arising in the case of the neutralisation of heparin with protamine sulphate; prevention of attacks in the case of unstable angina and TIA (transient ischaemic attacks) and in combinations with prostaglandins (e.g. $PGE_1$); improvement of the kidney function in the case of various types of glomerulonephrites, in the case of systemic lupus erythrematosus, in the case of nephrotoxicities induced by cyclosporin-A or other medicaments and as consequence of a hydronephrosis; prevention of ischaemic organ damages in the case of shock; prevention of rejection crises in the case of organ transplants, as well as maintenance of organ function in vitro and improvement of the organ blood supply after transplants, improvement of the kidney function or reduction of the side effects in the case of combinations with diuretics of various types of action (e.g. loop diuretics); improvement of peripheral circulatory disturbances, also in combination with prostacyclin (mimetics) and other prostaglandins (e.g. $PEG_1$); treatment and prophylaxis of gastrointestinal inflammations; prevention or weakening of asthma attacks and of bronchial hyperreactivity, also in combination with other anti-asthmatics (e.g. $\beta$-mimetics, theophylline and glucocorticosteroids); for the treatment of eclampsia and inhibition of premature labour pains; treatment of brain infarcts and of subarachnoid haemorrhage; treatment of arythmias. In principle, the active material can be administered in the form of solid medicinal forms, such as e.g. tablets, pellets or dragees, or also of liquid medicinal formulations as injection or infusion solution.

In the course of the development of an injection solution produced according to usual processes from the sodium salt of the active material, it has been shown that these solutions are not vein compatible. The active material was administered in a relatively high concentration of 25 to 50 mg/ml, whereby the solutions used for injection purposes display a pH value of 9.6 to 9.8. In the case of use of such injection solutions, in many cases parietal thromboses occurred at the point of injection which have indicated the interarterial incompatibility of these solutions. In one case, incompatibilities arose in the case of a dosage of 250 mg/10 ml of sodium 4-[2-benzenesulphonylamino)-ethyl]-phenoxyacetate in the case of the treatment of shock lung in humans.

Furthermore, the problem existed that the active material should be administered parenterally in a concentration as high as possible of up to 50 mg/ml in order to achieve a therapeutically sufficient dosaging. The free acid of the active material as such is relatively sparingly soluble in aqueous solution so that initially the corresponding sodium salt was used for the preparation of the solutions. The sodium salt possesses a solubility of about 55 mg/ml (164 mmol/l). This should itself suffice in order to produce the solutions suitably concentrated for injection purposes. However, such highly concentrated solutions which lie close to the upper solubility limit of the active material easily tend, in the case of comparatively long storage or in the case of heat sterilisations to be carried out, to form crystallisation nuclei which are present in the solution in the form of microscopically small particles or, in the case of comparatively long storage time, lead to turbidities of these solutions. These solutions are unsuitable for pharmaceutical use.

According to the directions given in the European Pharmacopoeia, particle-free injection or infusion solutions are required which are practically free from suspended particles. In the American and British Pharmacopoeias, limits are prescribed for the particle size which must not exceed certain values. In USP XXI, for example, the maximum permitted particle size per container amounts to 10–25 μm.

Thus, the task exists to make available pharmaceutical solutions of the active material for use as infusion or injection solutions which are readily vein compatible and are storage-stable for a comparatively long period of time without it coming to an increased particle formation or turbidity of the solution.

This task is thereby solved that a basic salt former is added to the aqueous solution or suspension of the active material. As suitable salt formers, there come into question basic amino acids, such as, for example, arginine, histidine or lysine; meglumine (N-methyl-glucamine) or tris-(hydroxymethyl)-aminomethane (TRIS ®, Trometamol ®).

These pharmaceutical solutions contain the active material in a concentration of 25–100 mg/ml (about 75–300 mmol/l, mole weight of the Na salt: 335.5 g/mol). The proportion of the basic salt former can vary within wide limits, depending upon the nature of the salt former used. Usually, the molar ratio between active material and basic salt former lies in the range of 1:0.1 to 1:2, preferably 1:0.5 to 1:1.5. However, an approximately equimolar amount is especially preferably used. If basic amino acids are used, then, as a rule, their concentration lies between 10 and 60 mg/ml (about 60 to 350 mmol/l), preferably at 13 to 50 mg/ml (about 70 to 320 mmol/l). Meglumine is used in an amount of 14 to 70 mg/ml (about 70 to 360 mmol/l), preferably of 16 to 64 mg/ml (about 80 to 330 mmol/l).

The final pharmaceutical form of administration of an injection solution in ampoule form contains the active material in an amount of 0.25 to 3 g, whereby the volume, according to need, can amount to between 5 ml and 10 ml. If the active material is to be infused, then concentrated solutions are preferably made commercially available which are used as addition to usual infusion solutions and these solutions are added shortly before administration. Such concentrated solutions contain the active material in a concentration of 25 to 100 mg/ml (about 70 to 300 mmol/l) in the case of a total volume of 10 ml and an amount of the active material of 0.25 to 1 g.

The amino acids usable as basic salt former can be used in the form of their racemates or of the optically-active forms, but preferably of the L-form.

The solutions according to the invention are also physiologically readily compatible in comparatively high concentrations of the active material. Furthermore, they withstand a heat treatment at 100° to 130° C. for the reduction of germs without noteworthy decomposition. Furthermore, these solutions have the advantage that they can, surprisingly, be stored over a comparatively long period of time at room temperature without turbidities arising or the active material changing chemically. According to previous experiences, such solutions are storage-stable over a period of time of at least three years.

Furthermore, it has, surprisingly, been found that the solutions according to the invention display an increased solubility in comparison with the sodium salt of the active material. Whereas the sodium salt of 4-[benzenesulphonylamino)-ethyl]-phenoxyacetic acid possesses a solubility of 55 mg/ml (164 mmol/l), in the case of the solutions prepared with basic salt formers, a distinctly higher solubility was found. In the case of the use of Trometamol ® as basic salt former, the solubility amounts to 78 mg/ml (233 mmol/l), the arginine salt possesses a solubility of 320 mg/ml (954 mmol/l) and the corresponding meglumine salt even a solubility of 430 mg/ml (1282 mmol/l). On the basis of this displacement of the solubility limit to distinctly higher values, it can be assumed therefrom that the tendency to the formation of visible or invisible suspended particles in the solution is relatively small. Furthermore, due to the increased solubility, the possibility exists to produce a concentrate of the active material which can be used as additive to conventional infusion solutions. Such highly concentrated solutions can readily be added to other infusion solutions which serve, for example, for the nutrition of the patients, wherewith the necessary infusion volume can be distinctly reduced in comparison with a separate administration.

The solutions according to the invention display a pH value of 8.0 to 8.4, whereby the basic salt formers are present in a buffer capacity of up to 0.1 val/l. In the case of the arginine salt of the active material, the equivalence point lies at pH 6.2, in the case of the meglumine salt at pH 7.4, whereas the sodium salt displays an equivalence point at pH 8.5.

In the case of the production of pH-stable solutions with the above-mentioned salt formers, it is also possible, by addition of larger amounts of bases beyond the equivalence point, to prevent a pH value decrease in the case of storage of the solutions. In the case of a constant pH value lying above the equivalence point, it is achieved that, due to the excess of basic components, the sparingly soluble acid of the active material cannot precipitate out and the particle formation is thereby suppressed.

On the basis of the above-given pH values of the injection solutions, as well as of the determined equivalence points of the individual active material salts, it can be deduced that the injection solution with the arginine salt displays the best compatibility since, surprisingly, it has the lowest pH value and the lowest equivalence point.

Because of the small buffer capacity of the basic salt formers used, the solutions according to the invention do not lead to significant pH value changes at the point of injection so that an almost painless intravenous or intraarterial use of these solutions is possible. Furthermore, such solutions can be administered undiluted. The buffer capacities of the basic salt formers used lies in the order of magnitude of 0.1 val/l, preferably 0.05 to 0.1 val/l. The solutions according to the invention can possibly be brought to the pH value of the blood of 7.4 by addition of an approximately equivalent amount of acid, for example hydrochloric acid. In the case of a normal ampoule content of 10 ml of injection solution with a content of about 0.1 val/l of the basic salt former, the addition of 10 ml of a 0.1 normal hydrochloric acid solution is sufficient in order to adjust the desired physiological pH value.

For the case that the solutions according to the invention are used as additive to infusion solutions in the form of concentrated solutions, the administration of the solution takes place unchanged via infusion pumps or diluted with appropriate infusion solutions, such as, for example, a 5% glucose solution of a 0.9% sodium chloride solution.

Furthermore, the solutions according to the invention can contain usual pharmacological adjuvants, such as e.g. mannitol, furthermore organic solubilising agents, such as e.g. polyethylene glycols, propylene glycol or other alkaloids, such as, perhaps, ethanol. Furthermore, further pharmaceutically active materials can be present in the solution insofar as the active materials are compatible with one another and a simultaneous administration is therapeutically expedient.

The following embodimental forms explain the invention by way of example without the inventive concept thereby being limited:

EXAMPLE 1

4-[2-(Benzenesulphonylamino)-ethyl]-phenoxyacetic acid injection solution of 250 mg/10 ml with addition of meglumine.

| | |
|---|---|
| 4-[2-(benzenesulphonylamino)-ethyl]-phenoxyacetic acid | 250.0 g (745 mmol) |
| meglumine | 160.0 g (820 mmol) |
| D-mannitol | 260.0 g |
| water for injection purposes ad | 10.0 l |

The solution suitable for filling into about 1000 ampoules is prepared as follows:

4-[2-(Benzenesulphonylamino)-ethyl]-phenoxyacetic acid is placed in 7 l of water for injection purposes with nitrogen gassing and suspended by vigorous stirring. The 4-[benzenesulphonylamino)-ethyl]-phenoxyacetic acid is dissolved by slow addition of the meglumine. A pH value of 8.2 to 8.4 is thereby adjusted. One dissolves the mannitol and makes up the solution to the end volume of 10 l and stirs up well. The solution is sterile-filtered over the usual filters, filled into ampoules and sterilised with pre- and post-gassing with nitrogen. The pH value of the so-obtained solution amounts to 8.3.

EXAMPLE 2

4-[2-(Benzenesulphonylamino)-ethyl]-phenoxyacetic acid injection solution of 250 mg/10 ml with addition of arginine.

| | |
|---|---|
| 4-[2-(benzenesulphonylamino)-ethyl]-phenoxyacetic acid | 250.0 g (745 mmol) |
| L-arginine | 140.0 g (804 mmol) |
| D-mannitol | 260.0 g |
| water for injection purposes ad | 10.0 l |

The solution suitable for filling into about 1000 ampoules is prepared as follows:

4-[2-(Benzenesulphonylamino)-ethyl]-phenoxyacetic acid is placed in 7 l of water for injection purposes with nitrogen gassing and suspended by vigorous stirring. The 4-[2-(benzenesulphonylamino)-ethyl]-phenoxyacetic acid is dissolved by slow addition of the arginine. A pH value of 8.0 to 8.2 is thereby adjusted. One dissolves the mannitol and makes up the solution to the end volume of 10 l and stirs up well. The solution is sterile-filtered over the usual filters, filled into ampoules and sterilised with pre- and post-gassing with nitrogen. The pH value of the so-obtained solution amounts to 8.1.

EXAMPLE 3

4-[2-(Benzenesulphonylamino)-ethyl]-phenoxyacetic acid infusion solution concentrate of 2 g/20 ml with addition of meglumine.

| | |
|---|---|
| 4-[2-(benzenesulphonylamino)-ethyl]-phenoxyacetic acid | 2000.0 g (5.96 mol) |
| meglumine | 1280.0 g (6.56 mol) |
| water for injection purposes ad | 20.0 l |

The solution suitable for the filling of about 1000 ampoules is prepared as follows:

4-[2-(Benzenesulphonylamino)-ethyl]-phenoxyacetic acid is placed in 15 l of water for injection purposes with nitrogen gassing and suspended by vigorous stirring. The 4-[benzenesulphonylamino)-ethyl]-phenoxyacetic acid is dissolved by the slow addition of the meglumine. The solution is made up to the end volume and well stirred up, sterile-filtered over the usual filters, filled into ampoules with pre- and post-gassing with nitrogen and sterilized. The pH value of the so-obtained infusion solution concentrate amounts to 8.3.

EXAMPLE 4

4-[2-(Benzenesulphonylamino)-ethyl]-phenoxyacetic acid infusion concentrate of 2 g/20 ml with addition of arginine.

| | |
|---|---|
| 4-[2-(benzenesulphonylamino)-ethyl]-phenoxyacetic acid | 2000.0 g (5.96 mol) |
| L-arginine | 1120.0 g (6.43 mol) |
| water for injection purposes ad | 20.0 l |

The solution suitable for the filling of about 1000 ampoules is prepared as follows:

4-[Benzenesulphonylamino)-ethyl]-phenoxyacetic acid is placed in 15 l of water for injection purposes with nitrogen gassing and suspended by vigorous stirring. The 4-[benzenesulphonylamino)-ethyl]-phenoxyacetic acid is dissolved by slow addition of the arginine. The solution is made up to the end volume and well stirred, sterile-filtered over the usual filters, filled into ampoules with pre- and post-gassing with nitrogen and sterilised. The pH value of the so obtained infusion solution concentrate amounts to 8.2. The titration basicity corresponds to 0.68 ml of 0.1 normal hydrochloric acid which are required per ampoule for the lowering of the pH value from 8.2 to 7.4.

EXAMPLE 5

4-[2-(Benzenesulphonylamino)-ethyl]-phenoxyacetic acid infusion solution concentrate of 1 g/10 ml with addition of arginine.

| | |
|---|---|
| 4-[2-(benzenesulphonylamino)-ethyl]-phenoxyacetic acid | 1000.0 g (2.98 mol) |
| L-arginine | 560.0 g (3.21 mol) |
| water for injection purposes ad | 10.0 l |

The solution suitable for the filling of about 1000 ampoules is prepared as follows:

4-[2-(Benzenesulphonylamino)-ethyl]-phenoxyacetic acid is placed in 15 l of water for injection purposes and suspended by vigorous stirring. The 4-[benzenesulphonylamino)-ethyl]-phenoxyacetic acid is dissolved by slow addition of the arginine. The solution is made up to the end volume and well stirred up, sterile-filtered over the usual filters, filled into ampoules with pre- and post-gassing with nitrogen and sterilised. The pH value of the so-obtained infusion solution concentrate amounts to 8.2. The titration basicity corresponds to 0.34 ml of 0.1 normal hydrochloric acid which are needed per ampoule for the lowering of the pH value from 8.2 to 7.4.

We claim:

1. A process for the preparation of a concentrated, pharmaceutical, at least 0.23 molar, solution of 4-[2-(benzenesulphonylamino)-ethyl]-phenoxyacetic acid as active material, comprising adding to an aqueous suspension of said active material at least one basic salt former selected from the group consisting of arginine, histidine, lysine, meglumine and tris-(hydroxymethyl)-aminomethane.

2. The process according to claim 1, wherein said basic salt former is used in an amount such that, after addition, the buffer capacity of the aqueous solution is up to 0.1 val/l.

3. The process according to claim 1, wherein said aqueous solution has a pH of 8.0 to 9.5.

4. The process according to claim 1, wherein the molar ratio between said active material and said basic salt former is 1:0.5 to 1:1.5.

5. A concentrated, storage-stable, pharmaceutical, at least 0.23 molar solution of a basic salt of an active material 4-[2-(benzenesulphonylamino)-ethyl]-phenoxyacetic acid with at least one of arginine, histidine, lysine, meglumine, or tris-(hydroxymethyl)-aminomethane to an aqueous suspension of said active material.

6. A solution according to claim 5, having a pH value of 8.0–9.5.

7. A pharmaceutical solution according to claim 5 for the preparation of storage-stable, readily compatible injection and infusion solutions.

8. A method of treating increased thrombocyte aggregation to inhibit the same which comprises infusing or injecting into a patient, having increased thrombocyte aggregation, a lipid shrinking amount, of an at least 0.23 m aqueous solution of 4-[2-(benzene-sulphonyl amino)-ethyl]-phenoxyacetic acid active material salt of at least one basic salt former selected from the group consisting of arginine, histidine, lysine, meglumine, and tris-(hydroxymethyl)-aminomethane.

9. The method of treatment according to claim 7 wherein said solution has a pH of about 8.0 to 9.5.

10. The method as claimed in claim 7 wherein the amount of said salt former in said solution is sufficient to provide a buffer capacity in said solution of up to about 0.1 val/l.

11. The method as claimed in claim 7 wherein the molar ratio between said active material and said basic salt former is about 1:0.5 to 1:1.5.

* * * * *